United States Patent [19]

Dollerup

[11] Patent Number: 5,314,909
[45] Date of Patent: May 24, 1994

[54] USE OF NON-STEROIDAL ANTIIFLAMMATORY AGENTS IN MACULAR DEGENERATION

[75] Inventor: Jens Dollerup, Lyngby, Denmark

[73] Assignee: Merck & Co., Inc., Rahway, N.J.

[21] Appl. No.: 32,366

[22] Filed: Mar. 17, 1993

[51] Int. Cl.$^5$ .................... A61K 31/40; A61K 31/21; A61K 31/19
[52] U.S. Cl. .................................. 514/420; 514/419; 514/513; 514/568; 514/912
[58] Field of Search ............... 514/420, 419, 513, 568, 514/912

[56] References Cited

U.S. PATENT DOCUMENTS 4,087,538  5/1978  Portnoff .............................. 424/274

OTHER PUBLICATIONS

Medline Abstract of Graefes Arch Clin Exp Ophthalmol 1992, 230(5) pp. 401–405, Peterson et al.
Medline Abstract of Klin Oczna, Jan. 1993, 95(1) pp. 44–46, Kaliska et al.

*Primary Examiner*—Zohreh Fay
*Attorney, Agent, or Firm*—Sylvia A. Ayler; Mark R. Daniel; Joseph F. DiPrima

[57] ABSTRACT

Topically applied non-steroidal antiinflammatory agents (NSAID's) are useful in the treatment of macular degeneration.

3 Claims, No Drawings

USE OF NON-STEROIDAL ANTIINFLAMMATORY AGENTS IN MACULAR DEGENERATION

Senile macular degeneration is one of the most common causes of reduction of vision after the age of 65. The condition is chronic with a progressive course. Even though some of the pathophysiological changes in the retina are known, the actual cause of the disease is not known, nor has there as yet been developed a treatment with convincing effects.

During the development of senile macular degeneration an increased permeability of the retinal pigment epithelium and the retinal capillaries are seen, with efflux of fluid and probably of tissue active substances which participate in the degeneration of tissue and the later scarification that takes place.

There is a well documented effect of Indomethacin in the treatment of cystoid macular oedema, a condition, as in senile macular degeneration, in which there is an increased permeability of the retinal capillaries and some destruction of retinal pigment epithelium.

Now with this invention, there is provided a novel method of treating macular degeneration by the topical administration to the eye of an effective amount of an NSAID.

The preferred NSAID for purposes of this novel method of treatment is indomethacin, but others of comparable antiinflammatory activity which are compatible with ophthalmic use are also useful. These include the following: diclofenac, ketorolac, flurbiprofen and the like.

The NSAID is applied topically to the eye in an ophthalmogically acceptable formulation in the form of an aqueous suspension or solution, an ointment, a gel or an aqueous solution which gels on contact with the eye. An aqueous solution or suspension is the preferred formulation and has about 1 to about 15 mg of NSAID per ml of formulation, preferably about 10 mg/ml.

In addition to the medicament, flocculating and deflocculating agents and water, conventional excipients and other materials are advantageously employed in preparing the ophthalmic suspension compositions of the present invention in accordance with good pharmaceutical practice. For example, the ophthalmic suspensions are sterile and preferably contain a bacteriological preservative to maintain sterility during use. Quarternary ammonium bacteriostats such as benzalkonium chloride may be used as well as phenyl mercuric acetate, phenyl mercuric nitrate, thimerosal, benzyl alcohol, or $\beta$-phenylethyl alcohol. These bacteriostats may suitably be used in a range of from 0.01 to 3.0 mg/ml and preferably 0.1 to 0.2 mg/ml of total suspension. An anti-oxidant may also be used to prevent oxidation of the medicament. Suitable anti-oxidants include sodium bisulfite, N-acetyl cysteine salts, sodium ascorbate, sodium metabisulfite, sodium acetone bisulfite and other acceptable anti-oxidants known to the pharmaceutical art. These anti-oxidants may suitably be used in a range of 0.1 to 10.0 mg/ml and preferably 0.2 to 3.5 mg/ml. In conjunction with the anti-oxidants, chelating agents such as disodium edetate may also be employed.

Viscosity inducing agents helpful in suspension characteristics of the composition, including cellulose derivatives such as hydroxymethyl cellulose, hydroxypropyl cellulose and methyl cellulose, may also be used in the formulation. For this purpose, one may use from 5.0 to 10.0 mg/ml and preferably from 1.5 to 3.5 mg/ml of such agents. Lecithin may also be used to provide helpful suspension characteristics for the ophthalmic suspension composition, being employed for this purpose in amounts of from 0.05 to 1.0 mg/ml of total suspension, and preferably from 0.1 to 0.4 mg/ml. A humectant is also sometimes used to help retain the water of the formulation in the eye. High molecular weight sugars are suitably used for this purpose such as sorbitol and dextrose in a concentration of from 0.1 to 10.0 mg/ml and especially 0.5 to 2.0 mg/ml. Finally, since the formulation is autoclaved to obtain initial sterility an autoclaving aid such as sodium chloride is normally added to the formulation.

The novel method of treatment of this invention comprises the topical ocular administration of 1 or 2 drops of the formulation 2 to 4 times a day.

A typical formulation for use in the novel method of treatment of this invention is a suspension of indomethacin, the preparation of which is described below:

The following procedures were followed in preparation of a 5 L batch of an acceptable ophthalmic suspension in accordance with the present invention, of 1-(p-chlorobenzoyl)-2-methyl-5-methoxy-3-indolyl acetic acid. The therapeutic dosage concentration of the total final batch was 10 mg/ml of medicament in the total suspension. However, dosage concentrations of the medicament of 5 mg/ml and 2.5 mg/ml may also be prepared following the same procedures, varying only the initial amount of medicament employed, proportionally to yield the resultant smaller dosage concentrations. A first mixture (I) was prepared by mixing in a 1250 ml bottle: 1 g sodium bisulfite, 30 g NaCl, 70 ml water, and 51.5 g 1-(p-chlorobenzoyl)-2-methyl-5-methoxy-3-indolyl acetic acid. A second mixture (II) was prepared by dissolving 1 g of lecithin in 225 ml water. A third (III) mixture was prepared by admixing 7.5 g of hydroxyethylcellulose in 1.5 L water, and bringing the total volume to 2.0 L after the initial mixture clarified. Finally, a fourth mixture (IV) of the remaining suspension ingredients was prepared by admixing 1.88 g polyoxyethylene (20) sorbitan monooleate, 1.0 g benzalkonium chloride, 12.5 g benzyl alcohol, 12.5 g $\beta$-phenylethyl alcohol, 50.0 g of sorbitol as aqueous solution, and 2.5 g disodium edetate. All four mixtures were sterilized by autoclaving for 30 minutes at 121° C. under 15 psig. Then, mixture II was added to I, and this mixture, in turn, was added to mixture III. Finally, mixture IV was added aseptically to the mixture of I, II and III by way of sterilizing membrane, and the total suspension volume was brought to 5 L with sterile water. The suspension was homogenized at 1500 psig and filled into containers.

What is claimed is:

1. A method of treating macular degeneration which comprises the topical ocular administration to a patient in need of such treatment of an effective amount of an NSAID.

2. The method of claim 1, wherein the NSAID is selected from the group consisting of indomethacin, diclofenac, ketorolac and flurbiprofen.

3. The method of claim 2 wherein the NSAID is indomethacin.

* * * * *